United States Patent
Bork et al.

(10) Patent No.: US 10,953,224 B2
(45) Date of Patent: *Mar. 23, 2021

(54) DEVICES AND METHODS FOR THE TREATMENT OF METABOLIC DISORDERS

(71) Applicant: Ethicon Endo-Surgery, Inc., Cincinnati, OH (US)

(72) Inventors: Toralf Bork, Enges (CH); Rocco Crivelli, Neuchatel (CH); Mathilde Miguras, Lelocle (CH); Martin Pfleiderer, Auvernier (CH); Yanik Tardy, Les-Geneveys-sur-Coffrane (CH); Jason L. Harris, Lebanon, OH (US); Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 42 days.

This patent is subject to a terminal disclaimer.

(21) Appl. No.: 16/225,215

(22) Filed: Dec. 19, 2018

(65) Prior Publication Data

US 2019/0143109 A1   May 16, 2019

Related U.S. Application Data

(63) Continuation of application No. 15/827,216, filed on Nov. 30, 2017, now Pat. No. 10,258,795, which is a
(Continued)

(51) Int. Cl.
*A61N 1/36* (2006.01)
*A61N 1/05* (2006.01)
*A61F 5/00* (2006.01)

(52) U.S. Cl.
CPC ........ *A61N 1/36007* (2013.01); *A61F 5/0026* (2013.01); *A61N 1/0509* (2013.01);
(Continued)

(58) Field of Classification Search
CPC .. A61N 1/0507; A61N 1/0509; A61N 1/0517; A61F 5/0026
See application file for complete search history.

(56) References Cited

U.S. PATENT DOCUMENTS

| 9,427,580 B2 | 8/2016 | Bork et al. |
| 9,855,424 B2 | 1/2018 | Bork et al. |

(Continued)

FOREIGN PATENT DOCUMENTS

WO   WO-2010143181 A1   12/2010

OTHER PUBLICATIONS

U.S. Appl. No. 13/825,459, U.S. Pat. No. 9,427,580, filed Mar. 30, 2012, Toralf Bork et al.

(Continued)

*Primary Examiner* — Joseph M Dietrich
(74) *Attorney, Agent, or Firm* — Mintz Levin Cohn Ferris Glovsky and Popeo, P.C.

(57) ABSTRACT

A system for stimulating the release of satiety hormone in a subject comprises a stimulus device which is implantable in the subject and adapted to apply an electrical stimulus to a tissue of a gastrointestinal system of said subject, and a detection device which is implantable in the subject and adapted to continuously monitoring at least one of a mechanical characteristic and an electrical characteristic of the subject to detect an ingestion of food by said subject, wherein the detection device cooperates with the stimulus device such that the stimulus device applies said electrical stimulus in response to a detected ingestion of food.

19 Claims, 7 Drawing Sheets

Related U.S. Application Data continuation of application No. 15/241,479, filed on Aug. 19, 2016, now Pat. No. 9,855,424, which is a continuation of application No. 13/825,459, filed as application No. PCT/EP2012/055831 on Mar. 30, 2012, now Pat. No. 9,427,580.

(52) U.S. Cl.
CPC . *A61F 2005/002* (2013.01); *A61F 2005/0016* (2013.01); *A61N 1/0517* (2013.01)

(56) References Cited

U.S. PATENT DOCUMENTS

| | | |
|---|---|---|
| 2007/0021736 A1 | 1/2007 | Johnson |
| 2008/0319504 A1 | 12/2008 | Loushin et al. |
| 2010/0056948 A1 | 3/2010 | Hornby et al. |
| 2010/0268306 A1 | 10/2010 | Maniak et al. |
| 2012/0277619 A1 | 11/2012 | Starkebaum et al. |
| 2013/0035740 A1 | 2/2013 | Sharma et al. |
| 2014/0277249 A1 | 9/2014 | Connor |
| 2018/0078762 A1 | 3/2018 | Bork et al. |

OTHER PUBLICATIONS

U.S. Appl. No. 15/241,479, U.S. Pat. No. 9,855,424, filed Aug. 19, 2016, Toralf Bork et al.
U.S. Appl. No. 15/827,216, filed Nov. 30, 2017, Toralf Bork et al.
International Search Report and Written Opinion for PCT Application No. PCT/EP2012/055831 dated Dec. 20, 2012 (22 pages).

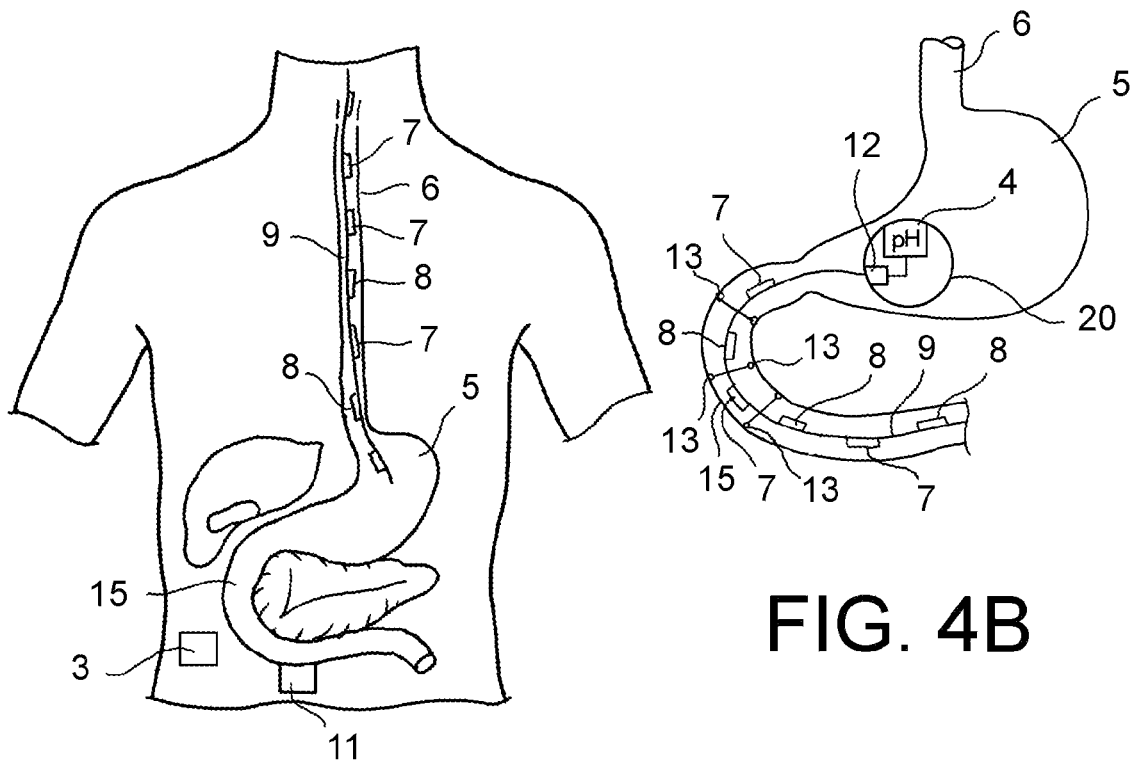
FIG. 4B
FIG. 4A
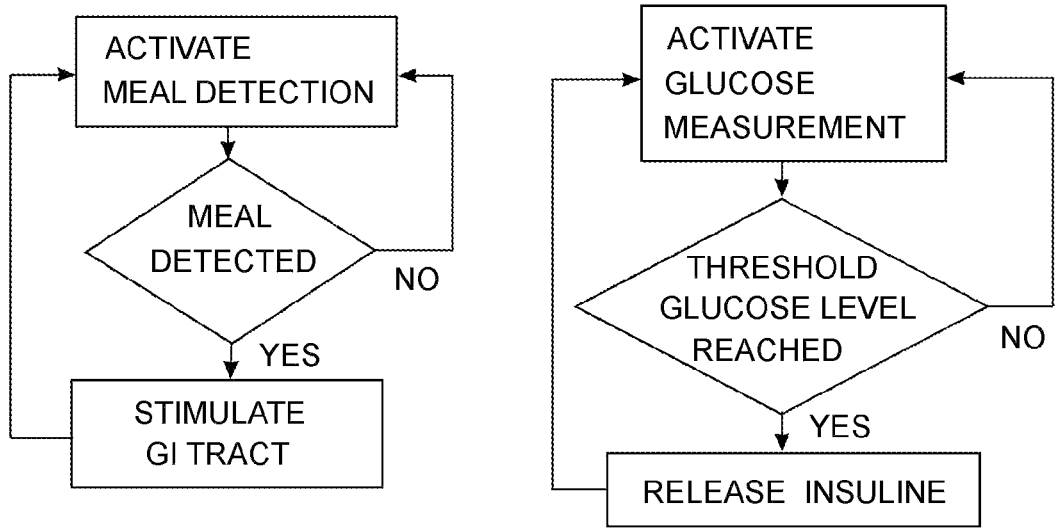
FIG. 5
FIG. 6

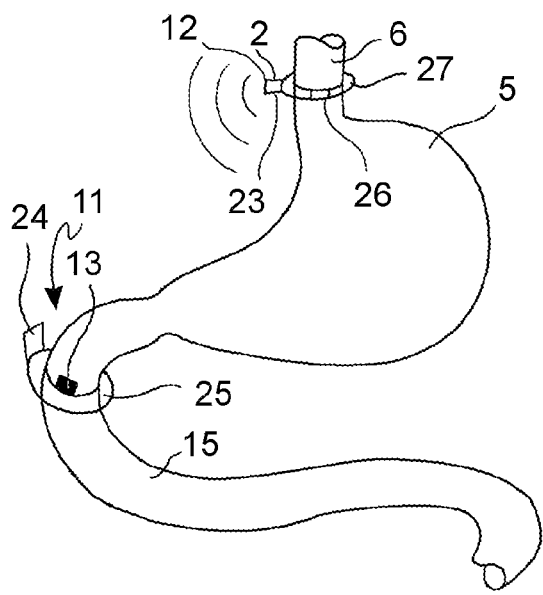
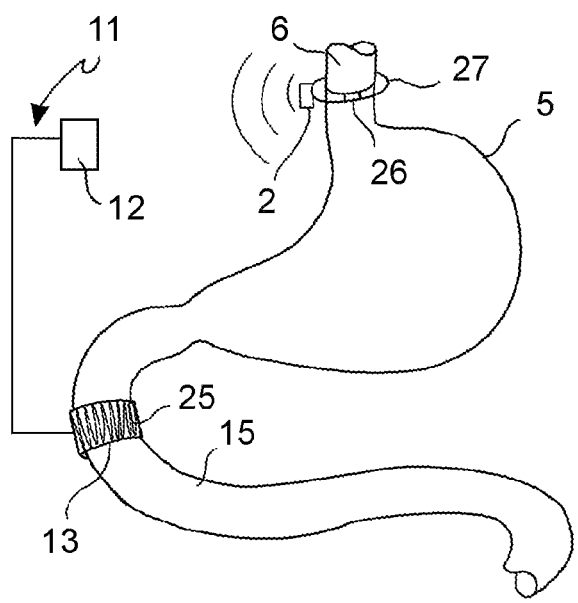
FIG. 10A  FIG. 10B
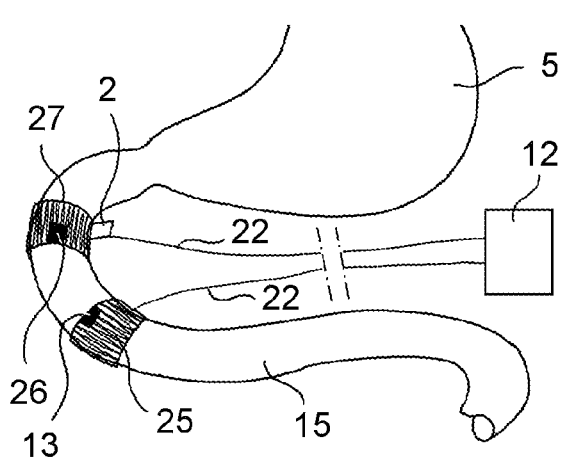
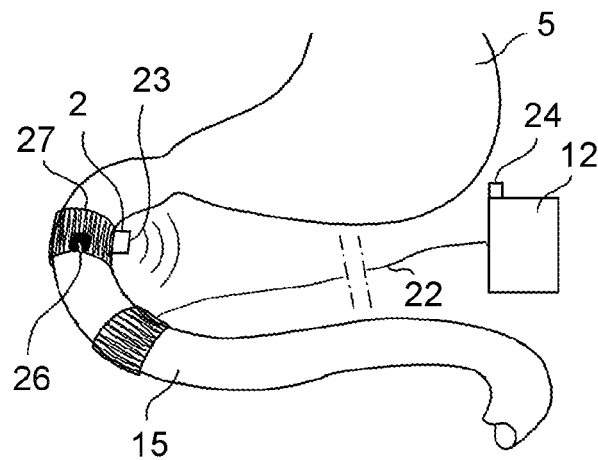
FIG. 11A  FIG. 11B
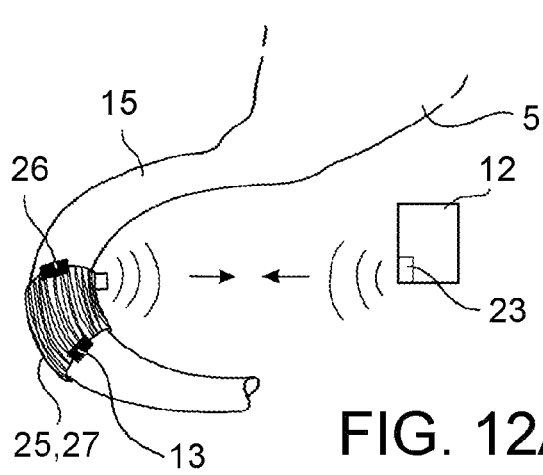
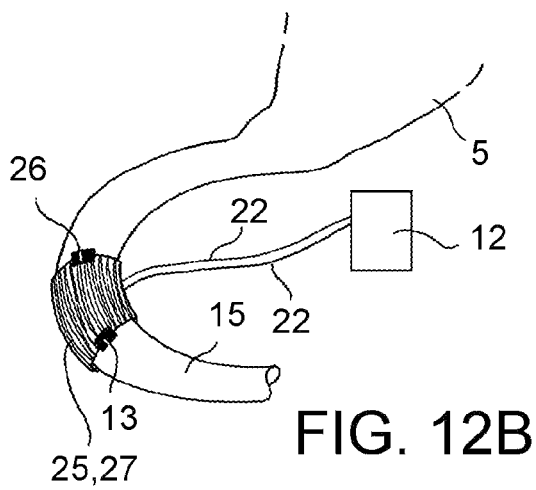
FIG. 12A  FIG. 12B

DEVICES AND METHODS FOR THE TREATMENT OF METABOLIC DISORDERS

CROSS REFERENCE

The present application is a continuation of U.S. application Ser. No. 15/827,216 entitled "Devices And Methods For The Treatment Of Metabolic Disorders" filed Nov. 30, 2017, now U.S. Pat. No. 10,258,795, which is a continuation of U.S. application Ser. No. 15/241,479 entitled "Devices And Methods For The Treatment Of Metabolic Disorders" filed Aug. 19, 2016, now U.S. Pat. No. 9,855,424, which is a continuation of U.S. application Ser. No. 13/825,459 entitled "Devices And Methods For The Treatment Of Metabolic Disorders" filed Nov. 3, 2014, now U.S. Pat. No. 9,427,580, which is a national stage application of PCT/EP2012/055831 entitled "Implantable System For Providing Electrical Stimulation In Response To Detecting An Ingestion Of Food" filed Mar. 30, 2012, which are hereby incorporated by reference in their entireties.

FIELD OF THE INVENTION

The present invention relates generally to devices and methods for the treatment of metabolic disorders using stimulation of the gastrointestinal tract. More specifically, the present invention relates to devices and methods for detecting meal or the passage or presence of food in the GI tract in order to allow for a timely and purposefully stimulation of the intestine in relation with the presence of food. The present invention further relates to a combined system for meal detection and electrical stimulation of the small intestine (duodenum, jejunum or ileum) aiming at an increased secretion of endogenous GLP-1 during meal intake.

BACKGROUND OF THE INVENTION

The human ability to store excess energy has contributed to an increased frequency of morbidly obese patients and those with Type 2 Diabetes. Patients having such conditions have increased morbidity and mortality resulting from associated co-morbidities, including cardiovascular disease and arthritis.

A sufficient release of Glucagon-Like Peptide (GLP-1), a known key hormone that regulates the body's glucose control hormone, is believed to alleviate Type 2 Diabetes and obesity. Normally, the presence of nutrients, which arise from a meal consisting of carbohydrates, fats and proteins, termed 'digesta' in the digestive tract, stimulates release of the body's own GLP-1 key hormone into the blood stream. Key hormones, released by specialized L-cells located in the mucosa, which is the innermost interior (luminal) wall of the intestines, coordinate the body's response to a meal. The hormones produce this effect by inducing a sense of fullness and cessation of eating (satiety), triggering the release of insulin to maintain proper glucose levels (incretin effect) and slowing the passage of contents through the digestive tract (delaying gastric emptying and slowing small intestinal transit). Altogether, these effects have been referred to as the "ileal brake" mechanism which involves both the hormones that play a role (such as PYY, GLP-1, and GLP-2, among others), as well as the multiplicity of effects of release of those hormones (gastric emptying, a feeling of fullness cessation of eating, triggering of insulin secretion).

An insufficient ileal brake, i.e., the inability of the body to release sufficient quantities of these hormones in response to a meal, is a contributory factor in obesity and Type 2 Diabetes. While in non-obese non-diabetic individuals fasting levels of GLP-1 are observed to be in the range of 5-10 pmol/L and to increase rapidly to 15-50 pmol/L after a meal, in T2D patients, the meal-related increase in GLP-1 is significantly less. The decreased insulin levels of such patients are attributable to an insufficient level of GLP-1. Similarly, also in obese subjects lower basal fasting hormone levels and smaller meal-associated rise of the hormone levels have been observed. Therefore, enhancing the body's endogenous levels of GLP-1 is believed to have impact on both obesity and diabetes.

There are known pharmaceutical means to increasing the endogenous active forms of GLP-1, e.g. by inhibition of its breakdown by dipeptidyl peptidase-4 (DPP-4) inhibitors, such as vildagliptin. In diabetic patients, improvement in glucose control is obtained by increasing the circulating levels of GLP-1 by vildagliptin.

As an alternative to pharmacological treatments, the most effective treatment for morbid obesity is bariatric surgery. A number of studies in patients after bariatric surgery suggest that there are increases in meal-related circulating GLP-1 levels after surgery, which contribute to the improvements in T2D and weight loss noted. However, bariatric surgery is perceived as a highly invasive measure recommended only for morbidly obese patients. A less invasive approach using a duodenal impermeable sleeve placed via an endoscope and fastened e.g. with a barbed metal anchor at the duodenal entrance has also shown to improve the glucose control.

It has been hypothesized that the manipulation of the intestine during and after surgery resulted in a stimulation of the mucosa which resulted in an increased release of the satiety hormone(s). US2010/0056948 describes a method of stimulating the release of satiety hormones in a subject comprising applying an electrical stimulus to a tissue in the gastrointestinal system of the subject contemporaneously with the contacting of L-cells of the tissue with a nutrient stimulus.

However, there remains still a need of an improved timing of the stimulation of the gastrointestinal system in relation with the food intake and the passage of the food bolus through the esophagus, stomach and intestine.

Currently available approaches for meal detection, such as HRV (heart rate variability) monitoring or detection of electrical signals in the duodenum are still to unspecific and indicate the ingestion of meal with too much delay for a precise electrical stimulation of the digestive system.

Also the proposed algorithms for so called artificial pancreas systems rely only on rough estimates of nutrition intake intervals which are indirectly derived from a continuous glucose metering and are calibrated to trigger a subcutaneous insulin administration in any case early enough to reach the blood stream in a timely manner.

SUMMARY OF THE INVENTION

In one aspect, the present invention provides devices and methods for detecting the food intake using one or a combination of esophageal high resolution manometry (HRM) and esophageal multichannel intraluminal impedance (MII). In another aspect, the invention provides devices and methods for detecting the food intake using one or a combination of detecting duodenal, gastric or esophageal electrical activity, detecting gastric pH and detecting esophageal and/or gastric movement and deformation.

In accordance with an aspect, duodenal, gastric or esophageal electrical activity can be detected using mucosal, serosal or cutaneous electrodes. Esophageal multichannel intraluminal impedance (MII) measuring may be used to monitor and record electrical impedance inside the esophagus in order to classify the type of meal through its electric conductivity. For this purpose multiple impedance transducers and associated pairs of electrodes may be arranged inside the esophagus along at least a portion of its length. Esophageal and gastric movements can be monitored and recorded by individual or multiple pressure transducers or strain gauges arranged at or inside the esophagus and/or stomach, along at least a portion of their length. Additionally, gastric pH can be detected by a pH meter arranged inside the stomach.

In accordance with an aspect, multiple pressure transducers and multiple pairs of electrodes are arranged along an elongate string shaped support, e.g. a catheter or a sleeve, extended endoluminally inside the esophagus and an esophageal contractive activity is monitored using HRM and a classification or identification of nutrition contents is accomplished on the basis of their conductivity using MII.

In accordance with a further aspect, one or a combination of a pressure transducer and an accelerometer are arranged near a jaw, specifically near a lower jaw of a patient, e.g. onboard an ear piece adapted to be fitted inside the ear canal, or onboard or inside a tooth implant, crown or bridge, and a characteristic chewing acceleration history and/or pressure history is monitored and used to detect a food intake.

In yet another aspect, a continuous glucose monitoring (CGM) is effected parallel to the detection of food intake and/or food passage, for a controlled insulin release from an insulin pump in dependency of the detected glucose levels.

In another aspect, the invention provides effecting an electrical stimulation of the digestive system, particularly an electrical stimulation of the mucosa of the small intestine (duodenum, jejunum, ileum) in response to a detection of food intake and/or food passage by the described food detection methods and devices. The electrical stimulation may be accomplished in dependency of food detection signals provided by the food detection devices and a preset electrical gut stimulation program.

In an aspect of the invention there is provided a control unit in signal communication with one or a combination of the food detection sensors, i.e. pressure transducer/s, strain gauge/s, pH meter, impedance transducer/s, accelerometer/s and glucose level detector/s, the control unit being adapted to elaborate the signals received from the food detection sensors to identify a condition of food intake and, in response to the identified condition of food intake, to generate a stimulus signal and provide the stimulus signal to an electrical stimulus device.

In accordance with an aspect, the stimulus device may comprise an electrical pulse generator and multiple electrodes which can be arranged at a tissue of the gastrointestinal system, particularly the small intestine.

In a further aspect, the food detection sensors, the control unit and the stimulus device may be incorporated in an integrated system or single integrated implantable device.

In accordance with a yet further aspect, the control unit may also generate and provide an insulin release signal to an insulin pump which determines the timing of insulin release and the quantity of released insulin in dependency of the signals received from the food detection sensors and from the continuous glucose monitoring sensor.

In this manner, a closed loop meal detection and intestinal electrical stimulation is provided for a purposeful and timely release of the satiety hormone GLP-1, resulting in an improved glycemic control and an appropriate feel of satiety in T2D and obese patients.

Moreover, the contemporaneous detection of both the event of food intake and the type of ingested food allows a more selective response with regard to electrical stimulation, insulin dosing and triggering of satiety and nausea enhancing measures.

In an aspect of the invention there is provided a method of stimulating the release of satiety hormone in a subject, the method comprising providing a stimulus device having a tissue engaging portion, placing the stimulus device in a target location of a gastrointestinal system of the subject such that the engaging portion engage a tissue of the gastrointestinal system, and moving the tissue engaging portion, thereby deforming the tissue of the GI system.

These and other aspects and advantages of the present invention shall be made apparent from the accompanying drawings and the description thereof, which illustrate embodiments of the invention and, together with the general description of the invention given above, and the detailed description of the embodiments given below, serve to explain the principles of the present invention.

BRIEF DESCRIPTION OF THE DRAWINGS

FIG. 4A illustrates a meal detection device of FIG. 1 or 2 endoluminally extended inside the esophagus of a patient;

FIG. 4B illustrates a meal detection device of FIG. 1 or 2 endoluminally extended inside the duodenum of a patient;

FIG. 5 is a schematic flow charts showing closed loop meal detection and gut stimulation and glucose level monitoring and insulin release which can be performed individually or contemporaneously;

FIG. 6 is a schematic flow charts showing closed loop meal detection and gut stimulation and glucose level monitoring and insulin release which can be performed individually or contemporaneously;

FIG. 10A illustrates a meal detection and electrical stimulation system for stimulating the release of satiety hormones in accordance with embodiments, the systems being deployed in the intraperitoneal space of a patient, with a meal detection device fastened from the outside around the esophagus and an electrical stimulation device fastened from the outside around the duodenum;

FIG. 10B illustrates a meal detection and electrical stimulation system for stimulating the release of satiety hormones in accordance with embodiments, the systems being deployed in the intraperitoneal space of a patient, with a meal detection device fastened from the outside around the esophagus and an electrical stimulation device fastened from the outside around the duodenum;

FIG. 11A illustrates a meal detection and electrical stimulation system for stimulating the release of satiety hormones in accordance with embodiments, the systems being deployed in the intraperitoneal space of a patient, with a meal detection device fastened from the outside around the duodenum and an electrical stimulation device fastened from the outside around the duodenum;

FIG. 11B illustrates a meal detection and electrical stimulation system for stimulating the release of satiety hormones in accordance with embodiments, the systems being deployed in the intraperitoneal space of a patient, with a meal detection device fastened from the outside around the duodenum and an electrical stimulation device fastened from the outside around the duodenum;

FIG. 12A illustrates a meal detection and electrical stimulation system for stimulating the release of satiety hormones in accordance with embodiments, the systems being deployed in the intraperitoneal space of a patient, with a meal detection and electrical stimulation device integrated in a single ring or arch fastened from the outside around the duodenum;

FIG. 12B illustrates a meal detection and electrical stimulation system for stimulating the release of satiety hormones in accordance with embodiments, the systems being deployed in the intraperitoneal space of a patient, with a meal detection and electrical stimulation device integrated in a single ring or arch fastened from the outside around the duodenum;

DETAILED DESCRIPTION OF EMBODIMENTS

Figure 1:
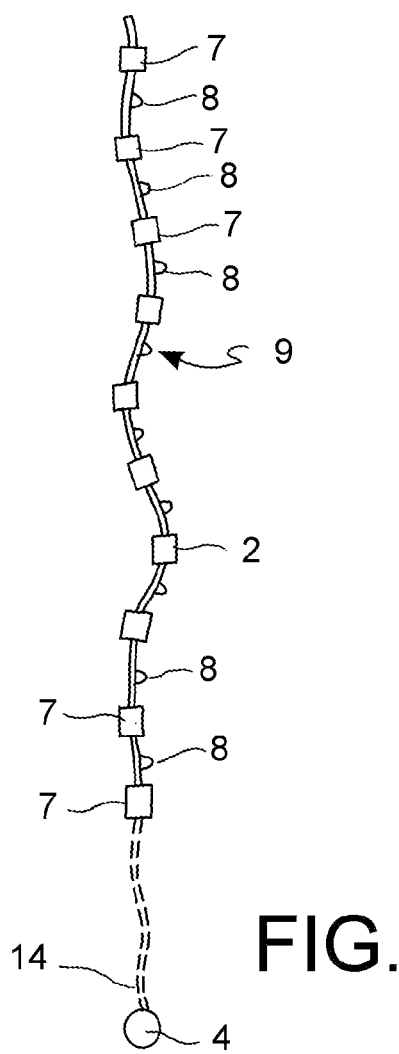
FIG. 1 illustrates a meal detection device in accordance with an embodiment.
Figure 2:
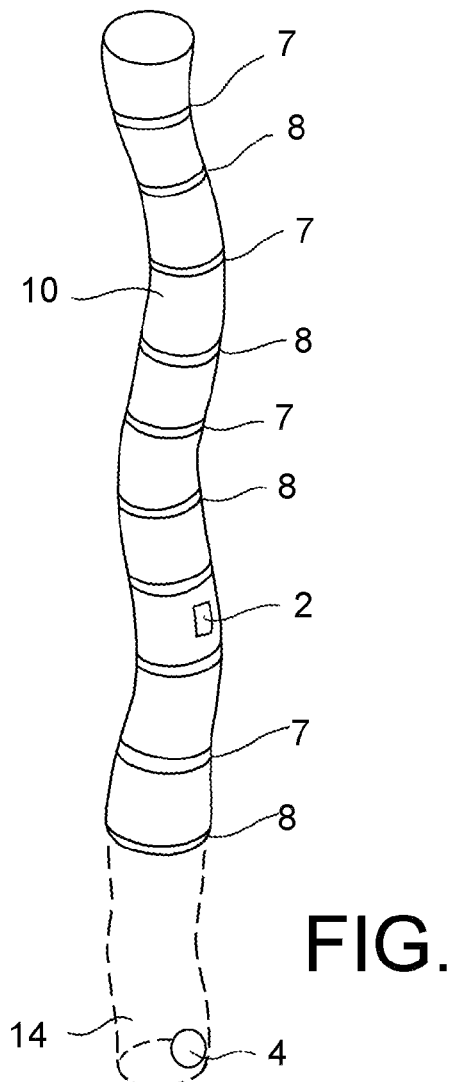
FIG. 2 illustrates a meal detection device in accordance with a further embodiment.

Referring to the drawings in which like numerals denote like anatomical structures and components throughout the several views, a method is provided for stimulating the release of satiety hormone, specifically GLP-1, in a human subject. In general terms, the method comprises continuous monitoring of at least one of a mechanical characteristic and an electrical characteristic of the subject to detect an ingestion of food by the subject, and applying an electrical stimulus to a tissue of a gastrointestinal system of the subject in response to a detected ingestion of food.

In accordance with an embodiment, both a mechanical and an electrical characteristic are continuously monitored in a gastrointestinal system of the subject, the gastrointestinal system including mouth, esophagus, stomach, small intestine and colon. In dependency from the monitored mechanical characteristic a decision is taken whether an ingestion of food has occurred and the ingested food is classified in dependency of the monitored electrical characteristic.

The nutrients contained in a food bolus can be identified through its electrical conductivity and the classification of the ingested food may be effected in dependency of the identified nutrients, such as carbohydrates, proteins, fats, vitamins, minerals, roughage, water.

One or any combination of a voltage, frequency, pulse duration, charge and place of application of the electrical stimulus at a tissue in the lumen of the gastrointestinal system may be determined and varied in dependency from a preset electrical gut stimulation program and from the classification of the ingested food.

In exemplary embodiments, the electrical stimulus may be applied and varied at a frequency of about 0.1 Hz to about 90 Hz, at a voltage of about 0.5 V to about 25 V, with a pulse duration of about 0.1 ms to about 500 ms. The electrical current may have a charge of about 1 μC to about 6000 μC, inclusive. The electrical stimulus may be applied to a mucosal tissue of the gastrointestinal system of the subject, e.g in a duodenum, jejunum or ileum.

In accordance with embodiments, the monitored mechanical characteristic may comprise one or a combination of a pressure, acceleration, lumen deformation, lumen extension or drag force exerted by the flow of contents through the GI tract.

The monitored electrical characteristic may comprise one or a combination of electrical currents in a tissue of the gastrointestinal system and electrical intraluminal impedance in a lumen of the gastrointestinal system, specifically in an esophagus or in a duodenum.

In accordance with an embodiment, parallel to the continuous monitoring of the mechanical and/or electrical characteristic a glucose concentration may be continuously monitored in the subject to detect glucose levels, and insulin is released in the subject in dependency of the detected glucose levels.

Within the present description of the invention, the expression "continuous monitoring" means a timed (for instance every few minutes or seconds") repetition of measuring or detecting a characteristic over an entire treatment period (of e.g. some days, weeks, months or even years) which yields a series of measured or detected values of the characteristic and provides a current value of the characteristic at any time during the treatment period.

Detailed Description of Embodiments of FIGS. 1 to 4a

In accordance with an embodiment (FIGS. 1 to 4A), a pressure inside the esophagus 6 of the subject is continuously monitored by means of esophageal high resolution manometry (HRM) to detect the passage of food through the esophagus 6. Contemporaneously, an electrical impedance is continuously monitored inside the esophagus 6 of the subject by means of multichannel intraluminal impedance (MII) and the detected food is classified in dependency of the monitored electrical impedance at the time of passage of the food bolus through the esophagus 6.

For this purpose, multiple pressure transducers 7 and multiple pairs of electrodes 8 are fastened to a flexible elongate support, e.g. a catheter 9 (FIG. 1) or a flexible esophageal sleeve 10 (FIG. 2) and the elongate support is endoluminally extended inside the esophagus 6 and anchored therein to stay in place. The esophageal high resolution manometry (HRM) is then carried out by means of the multiple pressure transducers 7 and the multichannel intraluminal impedance (MII) is carried out by means of the multiple pairs of electrodes 8.

The esophageal manometry may be carried out to perform both quantitative and qualitative measurements of esophageal pressure and peristaltic coordination. The elongate support sleeve 10 or catheter 9 may have a length of about 30 cm to 36 cm and carry a row of from 30 to 40 solid-state circumferential pressure sensors 7 spaced at constant intervals along the entire support length. Such an arrangement facilitates pressure assessment of the entire esophagus, from the pharynx to the LES. The pressure transducers 7 are linked to a control unit 2 (a microchip with a memory, a battery, and a data acquisition and elaboration software) for rapid interpretation of the monitored pressure values. The control unit 2 may be directly connected to the elongate support or, alternatively, the control unit 2 may be arranged remote from the elongate support.

Figure 3:
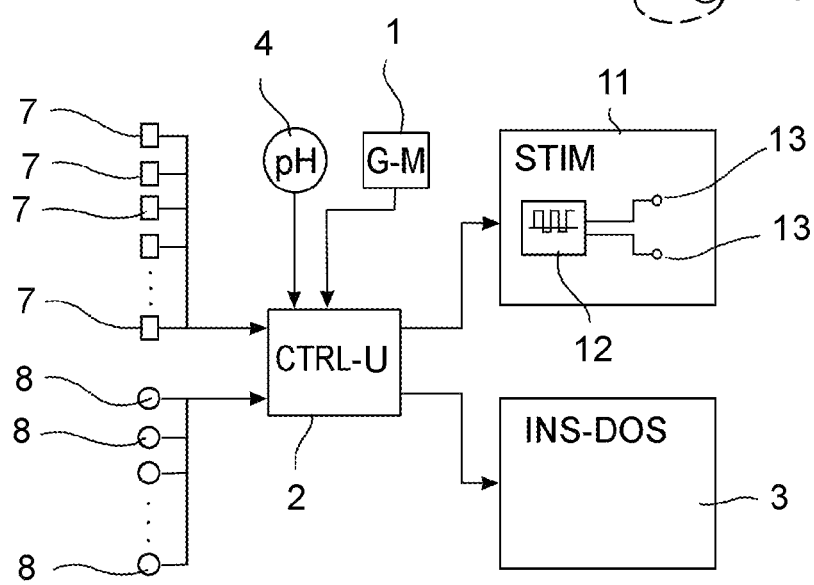
FIG. 3 shows a schematic block diagram of a meal detection and electrical stimulation system for stimulating the release of satiety hormones in accordance with an embodiment.

As illustrated in the block diagram in FIG. 3, the control unit 2 is in signal communication (by conductive wire or wireless, e.g. by an RF transmitter-receiver communication channel) with an electrical stimulus device 11.

The control unit 2 is adapted to elaborate the signals received from the food detection sensors (pressure transducers 7, impedance electrodes 8) to identify a condition of food intake and, in response to the identified condition of food intake, to generate a stimulus signal and provide the stimulus signal to the electrical stimulus device 11.

The stimulus device 11 may comprise an electrical pulse generator 12 and multiple stimulation electrodes 13 which are intended to be arranged at a tissue of the gastrointestinal system, particularly the small intestine.

Additionally, a continuous glucose monitoring (CGM) may be performed to determine current glucose levels, e.g. with measurement intervals in the range of 2 to 5 minutes. For this purpose a glucose sensor 1 may be placed in contact with bodily fluid of the patient, e.g. under the skin, and linked by a signal communication line to the control unit 2 or to an additional control unit in signal communication (by conductive wire or wireless, e.g. by an RF transmitter-receiver communication channel) with an insulin pump 3 with associated insulin reservoir.

In accordance with a further exemplary embodiment, additionally to the continuous monitoring of the mechanical and/or electrical characteristic and, if provided, to the glucose level monitoring, a pH may be continuously monitored inside the stomach 5 of the subject to detect an ingestion of food by the subject.

For this purpose a pH meter 4 may be placed inside the stomach 5 and linked by a signal communication line (by conductive wire or wireless, e.g. by an RF transmitter-receiver communication channel) to the control unit 2.

In an embodiment (FIGS. 1, 2 and 4A), the pH meter 4 is attached to a distal end portion 14 of the elongate support (esophageal sleeve 10 or esophageal catheter 9) which can extend inside the stomach 5 while a prevalent length of the elongate support extends inside the esophagus 6.

It will be readily understood that the same control unit 2 may also generate and provide an insulin release signal to the insulin pump 3 which determines the timing of insulin release and the dosage of released insulin in dependency of the signals received from the food detection sensors (pressure transducers 7, impedance electrodes 8, pH meter 4) and from the continuous glucose sensor 1.

In this manner, a closed loop meal detection and intestinal electrical stimulation is provided for a purposeful and timely release of the satiety hormone GLP-1, resulting in an improved glycemic control and an appropriate feel of satiety in T2D and obese patients.

Moreover, the contemporaneous detection of both the event of food intake and the type of ingested food allows a more selective response with regard to electrical stimulation, insulin dosing and triggering of satiety and nausea enhancing measures.

Detailed Description of Embodiments of FIG. 4 b

In accordance with an embodiment (FIG. 4B) the device described in relation with FIGS. 1 to 4A is anchored inside the stomach 5. The proximal end of the elongate support (catheter 9 or endoluminal sleeve 10) is anchored inside a stomach 5, e.g. by means of a balloon or coil shaped expandable anchoring body 20, and the elongate support is extended from inside the stomach 5 into the duodenum 15. In this manner the monitoring of the pressure and of the electrical impedance may be effected in the duodenum 15. Additionally the stimulus electrodes 13 are arranged at the elongate support (here a duodenal sleeve or a duodenal catheter) to engage the duodenal mucosa. The pH meter 4 and also the pulse generator 12 can be arranged at the anchoring body 20.

Figure 7:
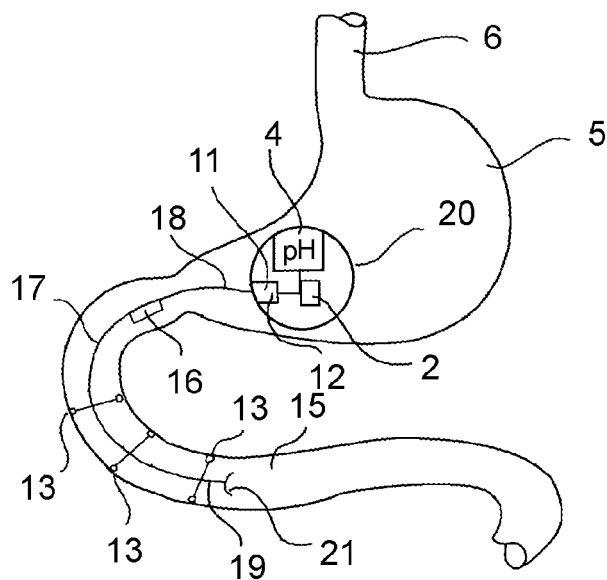
FIG. 7 illustrates a meal detection and electrical stimulation system for stimulating the release of satiety hormones in accordance with embodiments, the systems being endoluminally deployed inside the stomach and duodenum of a patient.

Detailed Description of Embodiments of FIG. 7

In accordance with a further embodiment (FIG. 7), the method comprises continuously monitoring a drag force of a flow inside a duodenum 15 of the subject in order to detect an ingestion of food by the subject.

For this purpose a flexible string shaped support medium 17 is provided and at least one strain gauge sensor 16 is attached to the support medium so that it can measure tensile forces transmitted by the support medium 17 in response to a flow of intestinal contents along the support medium 17. The ingestion of a meal is detected in dependency of the monitored flow variation inside the duodenum 15 during the transit of a food bolus.

The string shaped support medium 17 has a proximal end 18 and a distal end 19. The proximal end 18 of the support medium 17 is anchored inside a stomach 5, e.g. by means of a balloon or coil shaped expandable anchoring body 20, and the support medium 17 is extended from inside the stomach 5 into the duodenum 15. In order to increase the detectable pull at the support medium 17 an enlargement 21 may be formed distally to the strain gauge 16.

The strain gauge 16 is linked to a control unit 2 (a microchip with a memory, a battery, and a data acquisition and elaboration software) for rapid interpretation of the monitored drag force values. The control unit 2 may be advantageously housed in the anchoring body 20 and is in signal communication (by conductive wire or wireless, e.g. by an RF transmitter-receiver communication channel) with an electrical stimulus device 11.

The control unit 2 is adapted to elaborate the signals received from the food detection sensors (strain gauge 16 and, if provided, pH meter 4) to identify a condition of food intake and, in response to the identified condition of food intake, to generate a stimulus signal and provide the stimulus signal to the electrical stimulus device 11.

The stimulus device 11 may comprise an electrical pulse generator 12 which may be received in the anchoring body 20 and multiple stimulation electrodes 13 arranged at the support medium 17 in order to engage a mucosa of the duodenum 15.

Additionally, a continuous glucose monitoring (CGM) and controlled insulin release in dependency of the detected glucose levels may be performed by the previously described method steps and device arrangements.

In accordance with a further exemplary embodiment, additionally to the continuous monitoring of the mechanical and/or electrical characteristic and, if provided, to the glucose level monitoring, a pH may be continuously monitored inside the stomach 5 of the subject to detect an ingestion of food by the subject.

For this purpose a pH meter 4 may be placed inside the stomach 5 and linked by a signal communication line (by conductive wire or wireless, e.g. by an RF transmitter-receiver communication channel) to the control unit 2.

In an embodiment (FIG. 7), the pH meter 4 can be directly fastened to the proximal anchoring body 20 which is placed within the stomach 5.

Figure 8:
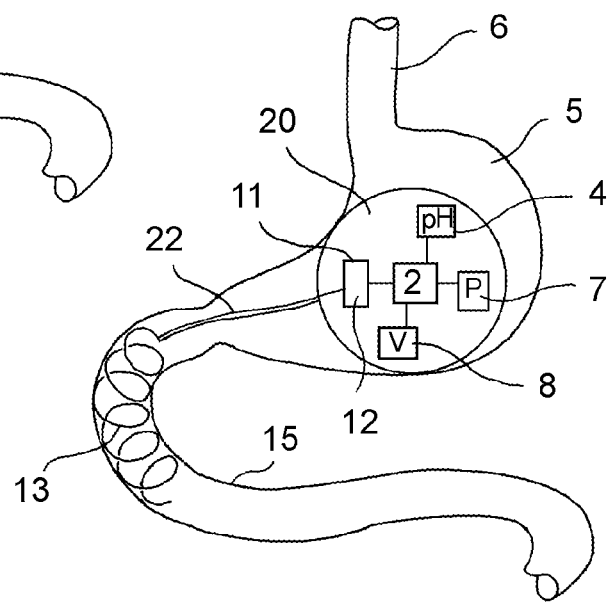
FIG. 8 illustrates a meal detection and electrical stimulation system for stimulating the release of satiety hormones in accordance with embodiments, the systems being endoluminally deployed inside the stomach and duodenum of a patient.
Figure 9B:
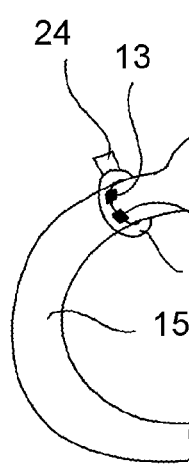
FIG. 9B illustrates an alternative arrangement of an electrical stimulation device positioned externally around the duodenum, the stimulation device being e.g. adapted to be used in connection with the gastric food detection system in FIG. 9A.
Figure 9A:
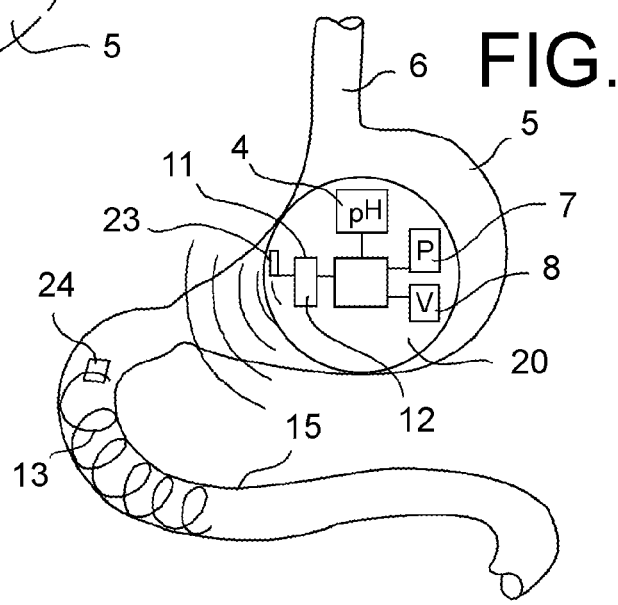
FIG. 9A illustrates a meal detection and electrical stimulation system for stimulating the release of satiety hormones in accordance with embodiments, the systems being endoluminally deployed inside the stomach and duodenum of a patient.

Detailed Description of Embodiments of FIGS. 8 to 9b

In accordance with an embodiment (FIGS. 8 through 9B), the method comprises continuously monitoring a pressure inside the stomach 5 of the subject and continuously monitoring an electrical current in a gastric wall of the subject in order to detect the ingestion of food by the subject.

For this purpose, a pressure sensor 7, at least a pair of electrodes 8 and a pH meter 4 are arranged on an expandable balloon shaped or coil shaped anchoring body 20, the anchoring body 20 is inserted inside the stomach 5 of the patient and then expanded such that the pressure sensor 7 and the electrodes 8 engage the gastric wall and the anchoring body 20 holds itself inside the stomach 5. After placement of the anchoring body 20, the pressure in the stomach 5 is monitored by means of the pressure sensor 7 and the electrical current in the gastric wall is monitored by means of the electrodes 8.

The pressure sensor 7 and the electrodes 8 are linked to a control unit 2 (a microchip with a memory, a battery, and a data acquisition and elaboration software) for rapid interpretation of the monitored pressure and current or electrical impedance values inside the stomach 5. The control unit 2 may be advantageously housed in the anchoring body 20 and is in signal communication (by conductive wire or wireless, e.g. by an RF transmitter-receiver communication channel) with an electrical stimulus device 11.

The control unit 2 is adapted to elaborate the signals received from the food detection sensors (pressure sensor 7, electrodes 8 and, if provided, pH meter 4) to identify a condition of food intake and, in response to the identified condition of food intake, to generate a stimulus signal and provide the stimulus signal to the electrical stimulus device 11.

The stimulus device 11 may comprise an electrical pulse generator 12 which may be received in the anchoring body 20 and one or more pairs of stimulation electrodes 13 provided at a distance from the anchoring body 20 and connected by electrical wires 22 (FIG. 8) to the pulse generator 12, so that the wires 22 can extend from the anchoring body 20 which is placed inside the stomach 5 through the pylorus down into the duodenum 15 where the electrodes 13 engage a mucosa of the duodenum 15. In this embodiment, the electrical wires 22 may accomplish both electrical energizing and mechanical anchoring of the electrodes 13.

FIGS. 8 and 9 show examples of coiled or corkscrew shaped electrode 13 arrangements adapted to engage the duodenal wall without obstructing the duodenum lumen.

Additionally, a continuous glucose monitoring (CGM) and controlled insulin release in dependency of the detected glucose levels may be performed analogously to the previously described method steps and device arrangements.

In accordance with a further exemplary embodiment, additionally to the continuous monitoring of the mechanical and/or electrical characteristic and, if provided, to the glucose level monitoring, a pH may be continuously monitored inside the stomach 5 of the subject to detect an ingestion of food by the subject.

For this purpose a pH meter 4 may be placed inside the stomach 5 and linked by a signal communication line (by conductive wire or wireless, e.g. by an RF transmitter-receiver communication channel) to the control unit 2.

In an embodiment (FIG. 7), the pH meter 4 can be directly fastened to the proximal anchoring body 20 which is placed within the stomach 5.

In accordance with a further variant (FIG. 9A) the pulse generator 12 is connected to an RF transmitter circuit and antennae 23 for a wireless transmission of the electrical stimulation energy and signals, and the electrode 13 arrangement comprises an RF receiving circuit and antenna 24 for a wireless reception of the stimulation energy and signals. In this embodiment, the wires 22 are not necessary, however, the electrode 13 arrangement must be directly anchored inside the duodenum 15 or connected to the anchoring body 20 by means of an anchoring wire.

In a yet further embodiment, an electrical stimulation band 25 adapted to be brought in a ring shaped configuration is (e.g. laparoscopically) arranged around the duodenum 15, and the stimulation electrodes 13 are provided on a radially internal surface of the stimulation band 25 to engage the duodenum 15 from outside. Also in this embodiment, the pulse generator 12 is connected to an RF transmitter circuit and antennae 23 for a wireless transmission of the electrical stimulation energy and signals, and the stimulation band 25 carries an RF receiving Detailed Description of Embodiments of FIGS. 10a to 12b In accordance with an embodiment, the method comprises continuously monitoring a hoop deformation (or, in other words: a change in circumference) caused by peristalsis of one of a duodenal wall and a distal esophageal wall of the subject in order to detect an ingestion of food by the subject.

For this purpose a band 27 is provided which is configured to be deformable from an open shape to a closed ring shape and lockable in the closed ring shape. A strain gauge 26 is arranged on the band 27 such that it can detect hoop stresses in the band 27 or variations of the (circumferential) length of the band 27. The band 27 is placed around one of a duodenum 15 and a distal esophagus 6 of the subject, e.g. by laparoscopy or open surgery.

Placement of the band 27 may also be effected by endolumenal transportation of the band 27 to the desired site for monitoring the hoop deformation, translumenal placement of the band 27 from inside the esophagus or duodenum through an incision in the lumen wall to its outside and extension of the band from outside the lumen around the lumen.

After placement of the band 27 around the duodenum 15 or esophagus 6, the hoop deformation of the duodenum 15 or esophagus 6 can be monitored by means of the strain gauge 26.

The strain gauge 26 is linked to a control unit 2 (a microchip with a memory, a battery, and a data acquisition and elaboration software) for rapid interpretation of the monitored hoop deformation. The control unit 2 may be directly connected to the band 27 or, alternatively, the control unit 2 may be arranged remote from the band 27.

The control unit 2 is in signal communication (by conductive wire or wireless, e.g. by an RF transmitter-receiver communication channel) with an electrical stimulus device 11.

The control unit 2 is adapted to elaborate the signals received from the food detection sensors (in the present embodiment: the strain gauge 26) to identify a condition of food intake and, in response to the identified condition of food intake, to generate a stimulus signal and provide the stimulus signal to the electrical stimulus device 11.

The stimulus device 11 may comprise an electrical pulse generator 12 and multiple stimulation electrodes 13 arranged at a tissue of the gastrointestinal system, particularly the small intestine.

In accordance with an embodiment, the stimulus device 11 includes a stimulus band 25 (similar to the one described in connection with FIG. 9B) which is configured to be deformable from an open shape to a closed ring shape and lockable in the closed ring shape. Multiple stimulation electrodes 13 are arranged at the stimulus band 25 such that they can contact a lumen (small intestine, duodenum) when the stimulus band 25 is placed around the lumen.

In an embodiment (FIG. 10A), the control unit 2 and the pulse generator 12 may be onboard the detecting band 27 and connected to an RF transmitter circuit and antennae 23 (onboard the detecting band 27) for a wireless transmission of the electrical stimulation energy and signals, and the stimulation band 25 carries an RF receiving circuit 24 and antenna for a wireless reception of the stimulation energy and signals.

In an alternative embodiment, the control unit 2 may be onboard the detecting band 27 and is connected to an RF transmitter circuit and antennae 23 (onboard the detecting band 27) for a wireless transmission of the stimulation signals to the pulse generator 12, and the stimulation band 25 carries the pulse generator 12 and an RF receiving circuit 24 and antenna for a wireless reception of the stimulation signals.

In a yet further embodiment (FIGS. 10B and 11B), the control unit 2 may be onboard the detecting band 27 and is connected to an RF transmitter circuit and antennae 23 (onboard the detecting band 27) for a wireless transmission of the stimulation signals to the pulse generator 12, and the pulse generator 12 with the RF receiving circuit 24 and antenna for a wireless reception of the stimulation signals is arranged remote from the stimulation band 25 and electrically connected thereto by conductive wire 22. In this case, the pulse generator 12 can be placed at a distance both from the detecting band 27 and from the stimulating band 25, e.g. inside the abdominal space of the patient.

In a further embodiment (FIG. 11A), the control unit 2 may be onboard the detecting band 27 and is connected by conductive wire 22 to the pulse generator 12, and the pulse generator 12 is connected by conductive wire 22 to the stimulation band 25. Also in this embodiment, the pulse generator 12 can be placed at a distance both from the detecting band 27 and from the stimulating band 25, e.g. inside the abdominal space of the patient.

In an embodiment (FIG. 12A), the pulse generator 12 is connected to an RF transmitter circuit and antennae 23 for a wireless transmission of the electrical stimulation energy and signals, and the stimulation band 25 carries an RF receiving circuit 24 and antenna for a wireless reception of the stimulation energy and signals.

In a preferred embodiment (FIGS. 12A, 12B), the detection band 27 and the stimulation band 25 are integrated in one single detection and stimulation band which can be placed around the duodenum 15 and which carries both the at least one strain gauge 26 for detecting the ingestion of food and the stimulus electrodes 13 for stimulating the GLP-1 secretion. Also in this embodiment, the control unit 2 and/or the pulse generator 12 may be directly onboard the band or at a distance to the band and connected by conductive wire or by wireless RF communication as described in connection with the previous embodiments.

Additionally, a continuous glucose monitoring (CGM) may be performed to determine current glucose levels and a dosage and release of insulin in the subject in dependency from the detected glucose levels may be performed by means of the previously described methods and devices.

In accordance with a further exemplary embodiment, additionally to the continuous monitoring of the hoop deformation of the esophageal wall or duodenal wall and, if provided, to the glucose level monitoring, a pH may be continuously monitored inside the stomach 5 of the subject to detect or confirm an ingestion of food by the subject.

For this purpose a pH meter 4 may be placed inside the stomach 5 and linked by a signal communication line (by conductive wire or wireless, e.g. by an RF transmitter-receiver communication channel) to the control unit 2.

Figure 13:
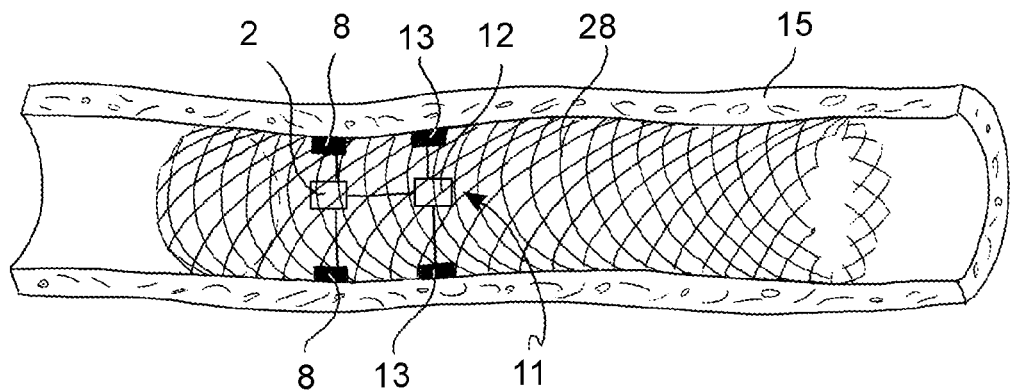
FIG. 13 illustrates a meal detection and electrical stimulation system for stimulating the release of satiety hormones in accordance with further embodiments.
Figure 14:
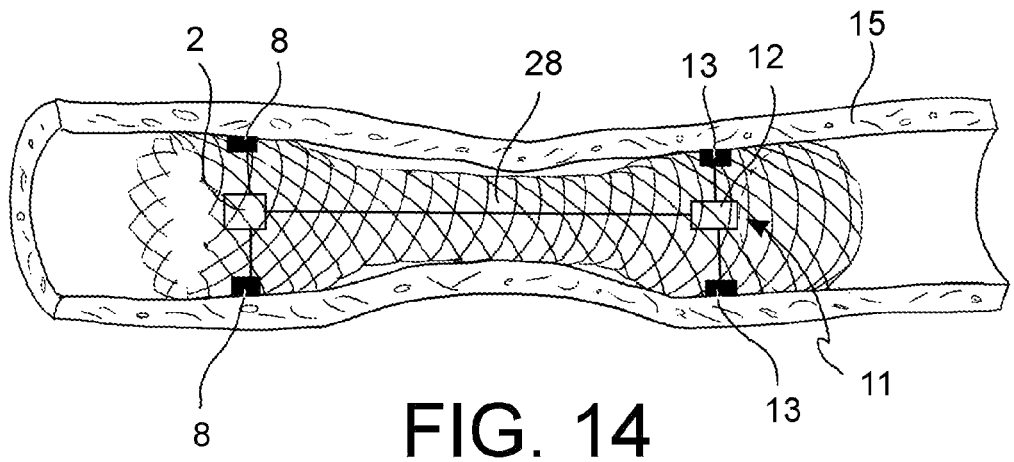
FIG. 14 illustrates a meal detection and electrical stimulation system for stimulating the release of satiety hormones in accordance with further embodiments.
Figure 15:
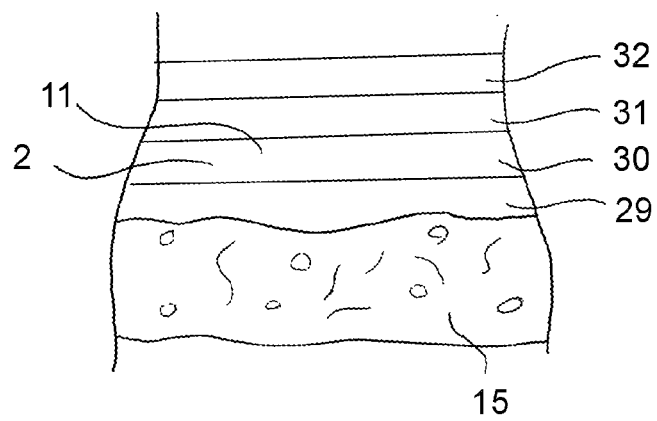
FIG. 15 is a schematic cross-section of a wall portion of the devices in FIGS. 13 and 14.
Figure 16:
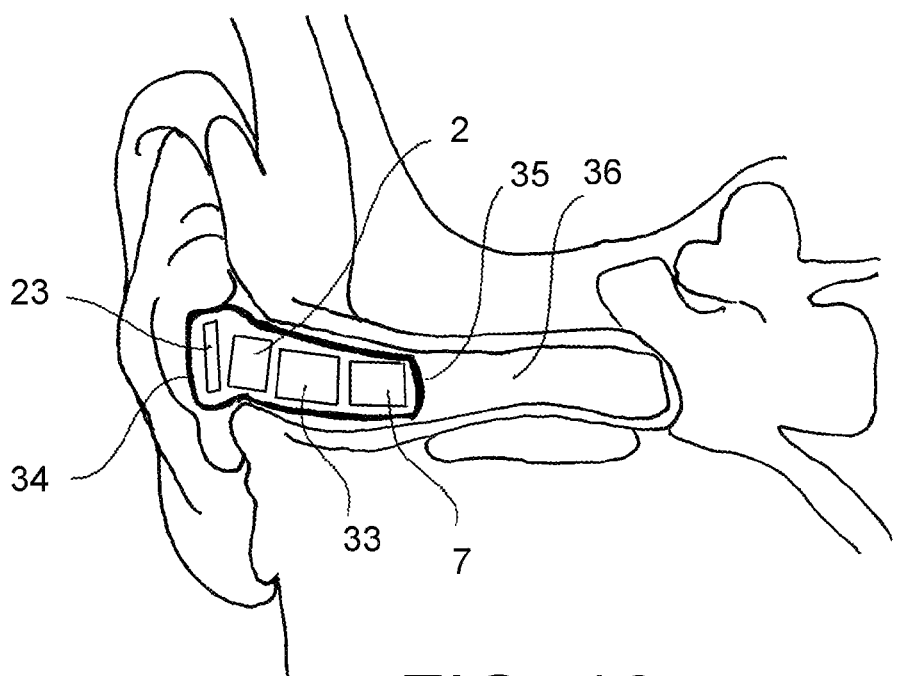
FIG. 16 illustrates a meal detection device placed in a patients ear in accordance with a further embodiment.

Detailed Description of Embodiments of FIGS. 13 to 15

In accordance with an embodiment (FIGS. 13, 14), the method may comprise continuously monitoring an electrical current in a duodenal wall of the subject in order to detect an ingestion of food by the subject.

For this purpose at least a pair of detecting electrodes 8 is arranged on an expandable tubular stent 28, e.g. a mesh shaped stent or a coil shaped stent, and the stent 28 is then placed inside the duodenum 15 of the subject and expanded therein such that the detecting electrodes 8 engage the duodenal wall and the stent remains anchored inside the duodenum 15. Then the electrical current in the duodenal wall can be monitored by means of the electrodes 8 which are linked to a control unit 2 (a microchip with a memory, a battery, and a data acquisition and elaboration software) for rapid interpretation of the monitored electrical activity. The control unit 2 may be directly connected to the stent 28 or, alternatively, the control unit 2 may be arranged remote from the stent 28.

The control unit 2 is in signal communication (by conductive wire or wireless, e.g. by an RF transmitter-receiver communication channel) with an electrical stimulus device 11.

The control unit 2 is adapted to elaborate the signals received from the food detection sensors (in the present embodiment: the detection electrodes 8) to identify a condition of food intake and, in response to the identified condition of food intake, to generate a stimulus signal and provide the stimulus signal to the electrical stimulus device 11.

The stimulus device 11 may comprise an electrical pulse generator 12 and multiple stimulation electrodes 13 arranged at a tissue of the gastrointestinal system, particularly the small intestine.

In a preferred embodiment, the entire stimulus device 11 or at least the stimulation electrodes 13 are directly connected to the same expandable stent 28, so that the release of the GLP-1 can be triggered in response to a detected food passage at the stent 28 without time delay at the very same location of the stent 28 within the duodenum 15.

In accordance with embodiments, the pulse generator 12 may be remote from the stent 28 and in wireless RF communication or electrical cable connection with the control unit 2 and/or the stimulus electrodes 13.

In accordance with an embodiment, the stent 28 is built as a multilayer stent (FIG. 15) having at least in one portion thereof an external electrode layer 29, e.g. a platinum layer coated with iridium oxide, an electronic circuit layer 30 beneath the electrode layer 29, which contains the control unit 2 and, if provided, the stimulation device 11 with an RF receiver circuit with antennae and/or an RF transmitter circuit with antenna, an insulation layer 31, e.g. in polyamide, provided beneath the circuit layer 30, and a structural layer 32 made from a shape memory alloy and arranged beneath the insulation layer 31.

Detailed Description of Embodiments of FIGS. 16 to 20

In accordance with an embodiment (FIGS. 16 to 20), the method may comprise continuously monitoring a chewing movement of the patient by monitoring at least one of an acceleration and a pressure at a lower jaw of the patient to detect an ingestion of food.

For this purpose an accelerometer 33 may be arranged inside an ear channel 36 of the subject and the acceleration at the lower jaw may be monitored by means of the accelerometer 33.

In accordance with an embodiment (FIGS. 16, 17) a head set or earpiece 34 is provided which has an insert portion 35 which can be fitted inside the ear channel 36. The accelerometer 33 is received in the insert portion 35 of the earpiece 34. The accelerometer 33 is linked to a control unit 2 (a microchip with a memory, a battery, and a data acquisition and elaboration software) for rapid interpretation of the monitored acceleration history. The control unit 2 may be directly received inside the insert portion 35 or housed in an external part of the headset or earpiece 34 or, alternatively, the control unit 2 may be arranged remote from the earpiece 34.

Figure 17:
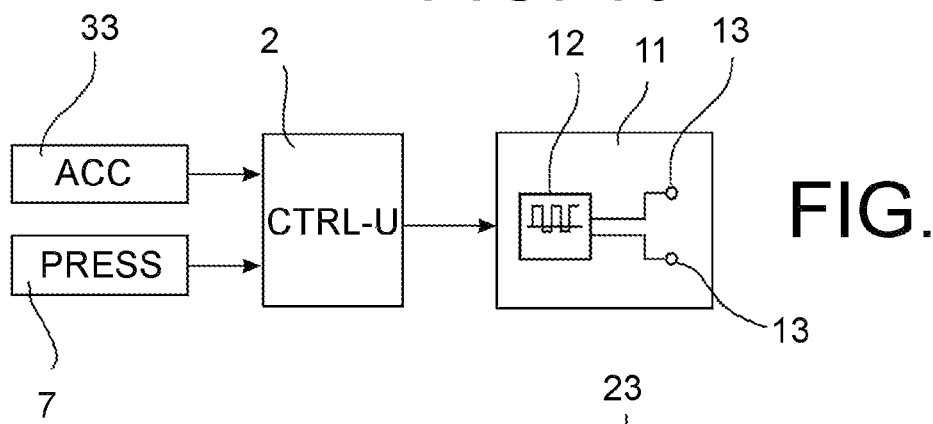
FIG. 17 shows a schematic block diagram of a meal detection and electrical stimulation system for stimulating the release of satiety hormones in accordance with an embodiment.
Figure 18:
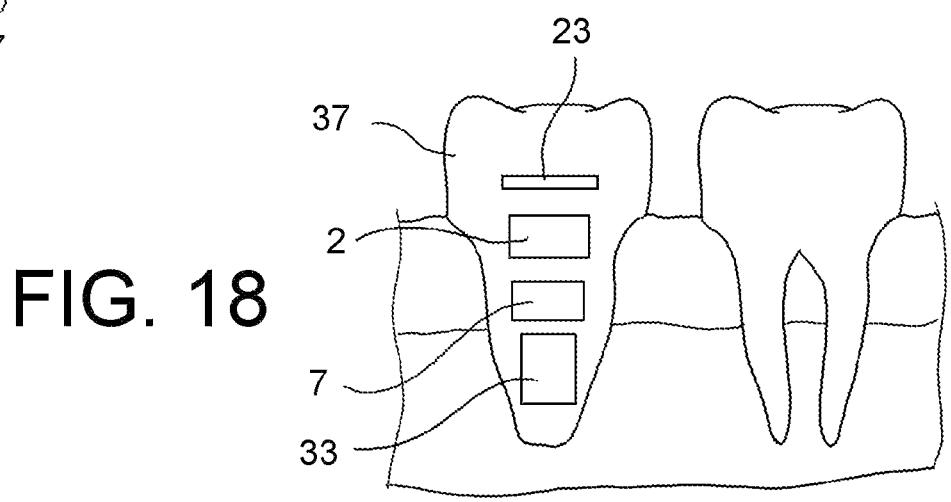
FIG. 18 illustrates a meal detection device placed on a patient's jaw in accordance with further embodiments.
Figure 19:
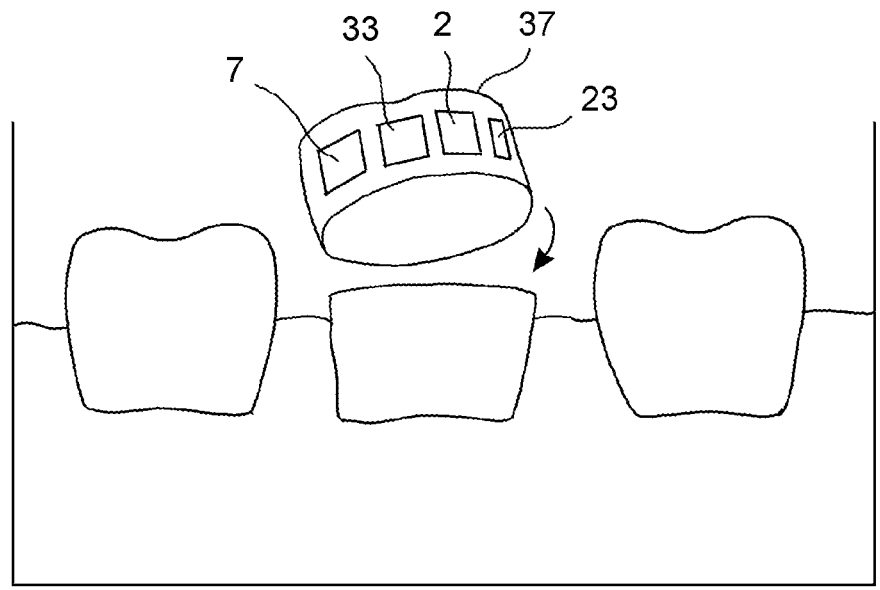
FIG. 19 illustrates a meal detection device placed on a patient's jaw in accordance with further embodiments.
Figure 20:
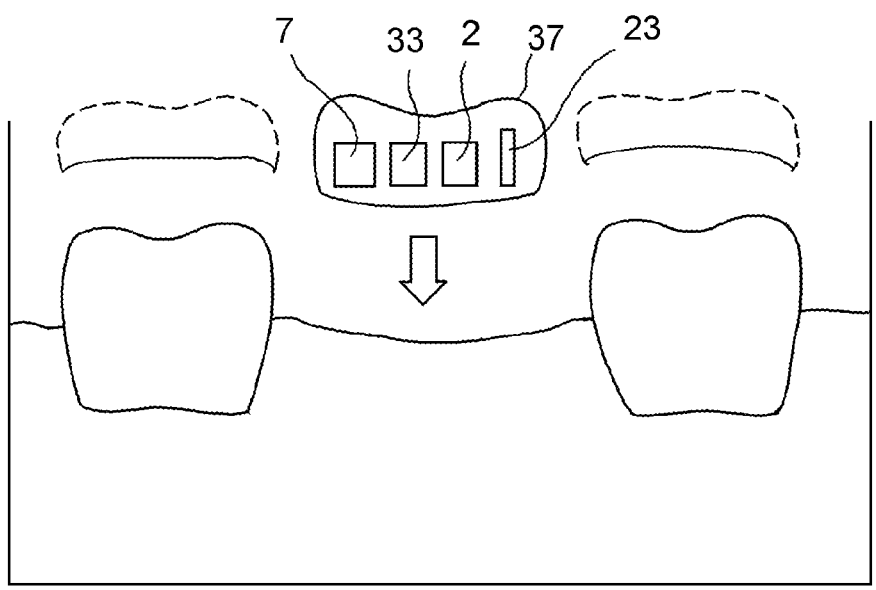
FIG. 20 illustrates a meal detection device placed on a patient's jaw in accordance with further embodiments.

As illustrated in the block diagram in FIG. 17 (which refers to both the embodiments of FIG. 16 and of FIGS. 18 to 20), the control unit 2 is in signal communication (by conductive wire or wireless, e.g. by an RF transmitter-receiver communication channel) with an electrical stimulus device 11.

The control unit 2 is adapted to elaborate the signals received from the food detection sensors (accelerometer 33) to identify a condition of food intake and, in response to the identified condition of food intake, to generate a stimulus signal and provide the stimulus signal to the electrical stimulus device 11.

The stimulus device 11 may comprise an electrical pulse generator 12 and multiple stimulation electrodes 13 arranged at a tissue of the gastrointestinal system, particularly the small intestine. The stimulus device 11 can be configured, implanted and operated as described in connection with the previous embodiments.

The control unit 2 is adapted to discern the differences between the jaw acceleration history during the ingestion of a meal from those during other activities like chewing a gum, swallowing saliva, speaking or singing, in order to avoid false positive scenarios. In response to the detection of an ingested meal, the control unit 2 will pilot the stimulus device 11 so that the latter applies an electrical pulse stimulation to the GI tract, particularly to the small intestine, thereby increasing the secretion of endogenous GLP-1. The earpiece 34 or head set may be powered by an onboard replaceable battery set.

In accordance with a yet further embodiment (FIGS. 17 to 20), the method step of detecting the ingestion of food comprises monitoring a pressure by means of a pressure transducer 7 arranged inside a tooth implant 37 directly at the lower jaw of the patient. Alternatively or in combination, an acceleration may be monitored by means of an accelerometer 33 arranged inside the tooth implant 37.

For this purpose the tooth implant 37 may be configured as a crown or capsule implant (FIG. 19), a bridge implant (FIG. 20) or a tooth root implant (FIG. 18) and receives the pressure transducer 7 and/or the accelerometer 33. Also in this embodiment, the accelerometer 33 and/or the pressure sensor 7 is linked to a control unit 2 (a microchip with a memory, a battery, and a data acquisition and elaboration software) for rapid interpretation of the monitored pressure and/or acceleration history. The control unit 2 may be directly received inside the tooth implant 37 or, alternatively, the control unit 2 may be arranged remote from the earpiece 34. For the wireless signal transmission between the control unit and the food detection sensors and/or the stimulus device, an RF transmitter circuit and antennae 23 and a corresponding RF receiving circuit and antenna are provided.

As illustrated in the block diagram in FIG. 17, the control unit 2 is in signal communication (by conductive wire or wireless, e.g. by an RF transmitter-receiver communication channel) with an electrical stimulus device 11.

The control unit 2 is adapted to elaborate the signals received from the food detection sensors (accelerometer 33, pressure sensor 7) to identify a condition of food intake and, in response to the identified condition of food intake, to generate a stimulus signal and provide the stimulus signal to the electrical stimulus device 11.

The dental implant 37 is implanted in the mouth of the patient, preferably in the lower jaw, by known dental procedures. The control unit 2 is adapted to discern the differences between the jaw acceleration history and/or the chewing pressure history during the ingestion of a meal from those during other activities like chewing a gum, swallowing saliva, speaking or singing, in order to avoid false positive scenarios. In response to the detection of an ingested meal, the control unit 2 will pilot the stimulus device 11 so that the latter applies an electrical pulse stimulation to the GI tract, particularly to the small intestine, thereby increasing the secretion of endogenous GLP-1.

All described embodiments of the present invention provide a closed loop meal detection and intestinal electrical stimulation for a purposeful and timely release of the satiety hormone GLP-1, resulting in an improved glycemic control and an appropriate feel of satiety in T2D and obese patients.

Although preferred embodiments of the invention have been described in detail, it is not the intention of the applicant to limit the scope of the claims to such particular embodiments, but to cover all modifications and alternative constructions falling within the scope of the invention.

The invention claimed is:

1. A medical system, comprising:
   a sensor configured to gather data regarding a characteristic of a gastrointestinal tract of a subject, the characteristic being at least one of pH in the gastrointestinal tract, pressure in the gastrointestinal tract, acceleration in the gastrointestinal tract, tensile force in the gastrointestinal tract, deformation of a lumen of the gastrointestinal tract, and drag force exerted by a flow of contents through the gastrointestinal tract;
   a second sensor configured to gather data regarding an impedance of tissue of the subject; and
   a controller configured to
      receive a signal from the sensor indicative of the data,
      use the signal to determine if food is present in the gastrointestinal tract,
      in response to determining presence of food in the gastrointestinal tract, cause a stimulus to be delivered to the gastrointestinal tract, wherein the stimulus includes an electrical stimulus,
      receive a second signal from the second sensor indicative of the data,
      use the second signal to classify a type of food present in the gastrointestinal tract, and
      use the classified type to determine at least one of a voltage, a frequency, a pulse duration, a charge, and a place of application of the electrical stimulus.

2. The system of claim 1, further comprising a plurality of electrodes configured to provide the electrical stimulus to the gastrointestinal tract.

3. The system of claim 2, further comprising a generator configured to generate electrical energy and transmit the generated electrical energy to the plurality of electrodes.

4. The system of claim 1, wherein the controller is configured to, in response to detecting that food is not present in the gastrointestinal tract, waiting to receive another signal from the sensor indicative of subsequently gathered data.

5. The system of claim 1, wherein the sensor is configured to continuously gather data and to continuously communicate the gathered data to the controller.

6. The system of claim 1, further comprising a plurality of electrodes configured to provide the stimulus and to be implanted in the subject.

7. The system of claim 6, further comprising a generator configured to generate electrical energy and transmit the generated electrical energy to the plurality of electrodes.

8. The system of claim 1, wherein the characteristic includes pH in the gastrointestinal tract and at least one other of pressure in the gastrointestinal tract, acceleration in the gastrointestinal tract, tensile force in the gastrointestinal tract, deformation of a lumen of the gastrointestinal tract, and drag force exerted by a flow of contents through the gastrointestinal tract.

9. The system of claim 1, wherein the characteristic includes at least one of pressure in the gastrointestinal tract, acceleration in the gastrointestinal tract, deformation of a lumen of the gastrointestinal tract, and drag force exerted by a flow of contents through the gastrointestinal tract.

10. A medical system, comprising:
    a sensor configured to gather data regarding at least one of a mechanical characteristic of a gastrointestinal tract of a subject and an electrical characteristic of the gastrointestinal tract of a subject;
    a second sensor configured to gather data regarding an impedance of tissue of the subject;
    a plurality of electrodes configured to be implanted in the subject; and
    a controller configured to
       receive a signal from the sensor indicative of the data,
       use the signal to determine if food is present in the gastrointestinal tract,
       in response to determining presence of food in the gastrointestinal tract, cause the plurality of electrodes to deliver an electrical stimulus to the gastrointestinal tract,
       receive a second signal from the second sensor indicative of the data,
       use the second signal to classify a type of the food, and
       use the classified type to determine at least one of a voltage, a frequency, a pulse duration, a charge, and a place of application of the electrical stimulus.

11. The system of claim 10, further comprising a generator configured to generate electrical energy and transmit the generated electrical energy to the plurality of electrodes.

12. The system of claim 10, wherein the controller is configured to, in response to determining that food is not present in the gastrointestinal tract, wait to receive another signal from the sensor indicative of subsequently gathered data.

13. The system of claim 10, wherein the sensor is configured to continuously gather data and to continuously communicate the gathered data to the controller.

14. The system of claim 10, wherein the sensor is configured to gather data regarding at least the mechanical characteristic, and the mechanical characteristic includes at least one of pressure in the gastrointestinal tract, acceleration in the gastrointestinal tract, deformation of a lumen of the gastrointestinal tract, and drag force exerted by a flow of contents through the gastrointestinal tract.

15. The system of claim 10, wherein the sensor is configured to gather data regarding at least the electrical characteristic, and the electrical characteristic includes at least one of pH, current, and impedance.

16. A medical system, comprising:
    a sensor configured to continuously gather data regarding at least one of pressure in a gastrointestinal tract of a subject and acceleration in the gastrointestinal tract;
    a controller configured to
       receive a signal from the sensor indicative of the data,
       use the signal in comparing the characteristic with historic data regarding the characteristic in the gastrointestinal tract of the subject,
       determine whether food intake occurred based on the comparison, and
       in response to determining that food intake occurred, cause an electrical stimulus to be delivered to the gastrointestinal tract; and
    a plurality of electrodes configured to provide the electrical stimulus.

17. The system of claim 16, wherein the controller is configured to, in response to determining that food intake did not occur, waiting to receive another signal from the sensor indicative of subsequently gathered data.

18. The system of claim 16, further comprising a second sensor configured to gather data regarding an impedance of tissue of the subject;
   wherein the controller is configured to
      receive a second signal from the second sensor indicative of the data,
      use the second signal to classify a type of the food, and
      use the classified type to determine at least one of a voltage, a frequency, a pulse duration, a charge, and a place of application of the electrical stimulus.

19. The system of claim 16, further comprising a generator configured to generate electrical energy and transmit the generated electrical energy to the first and second electrodes.

* * * * *